US012625126B2

(12) United States Patent　　　(10) Patent No.:　US 12,625,126 B2
Roy et al.　　　(45) Date of Patent:　May 12, 2026

(54) METHOD OF MODELLING OF A MATERIAL

(71) Applicant: AIRBUS SAS, Blagnac (FR)

(72) Inventors: Rohan Roy, Bristol (GB); Trupti Kulkarni, Bristol (GB)

(73) Assignee: AIRBUS (S.A.S.), Blagnac (FR)

( * ) Notice:　Subject to any disclaimer, the term of this patent is extended or adjusted under 35 U.S.C. 154(b) by 1204 days.

(21) Appl. No.: 17/512,453

(22) Filed:　　Oct. 27, 2021

(65)　　　　Prior Publication Data

US 2022/0170901 A1　　Jun. 2, 2022

(30)　　Foreign Application Priority Data

Nov. 30, 2020　(IN) .............................. 202011052043

(51) Int. Cl.
*G01N 33/204*　　(2019.01)
*B22F 10/80*　　(2021.01)
*C22C 14/00*　　(2006.01)
(52) U.S. Cl.
CPC ........... *G01N 33/204* (2019.01); *B22F 10/80* (2021.01); *C22C 14/00* (2013.01)
(58) Field of Classification Search
None
See application file for complete search history.

(56)　　　　References Cited

U.S. PATENT DOCUMENTS 6,731,996 B1 * 5/2004 MacEwen ................. C22F 3/00
702/42

OTHER PUBLICATIONS

Lim, Hojun, et al. "Incorporating physically-based microstructures in materials modeling: Bridging phase field and crystal plasticity frameworks." Modelling and Simulation in Materials Science and Engineering 24.4 (2016): 045016. (Year: 2016).*
Choi, Shi-Hoon, and Jae Hyung Cho. "Primary recrystallization modelling for interstitial free steels." Materials Science and Engineering: A 405.1-2 (2005): 86-101 (Year: 2005).*
Mandal, Sudipto, et al. "Simulation of plastic deformation in Ti-5553 alloy using a self-consistent viscoplastic model." International Journal of Plasticity 94 (2017): 57-73. (Year: 2017).*
Zhang, C., et al. "Effect of realistic 3D microstructure in crystal plasticity finite element analysis of polycrystalline Ti—5Al-2.5 Sn." International Journal of Plasticity 69 (2015): 21-35 (Year: 2015).*

(Continued)

*Primary Examiner* — Kamini S Shah
(74) *Attorney, Agent, or Firm* — Nixon & Vanderhye, PC

(57)　　　　ABSTRACT

A method of predicting a mechanical property of a material subjected to a transformation process is disclosed including a modelling step, wherein a microstructural model of the material is created, a simulation step, wherein the microstructural model of the material is virtually subjected to a transformation process (such as a heat treatment process), a generation step, wherein at least one micro-scale model configured for predicting at least one mechanical property of the material is generated, and a virtual mechanical characterisation, wherein at least one mechanical property of the material is predicted. Advantageously, by implementing this method it has been found that lead times incurred when developing new material transformation processes can be reduced.

20 Claims, 6 Drawing Sheets

(56)  References Cited

OTHER PUBLICATIONS

Kumara, C., Deng, D., Hanning, F. et al. Predicting the Microstructural Evolution of Electron Beam Melting of Alloy 718 with Phase-Field Modeling. Metall Mater Trans A 50, 2527-2537 (2019) (Year: 2019).*

Shi, Rongpei, Yunzhi Wang, and Dong Wang. "Modeling and simulation of microstructure evolution during heat treatment of titanium alloys." Heat Treating of Nonferrous Alloys. ASM international, 2016. 573-603 (Year: 2016).*

Choi, Shi-Hoon et al. "Primary Recrystallization Modelling for Interstitial Free Steels", Materials Science and Engineering, vol. 405, No. 1-2, pp. 86-101, Sep. 25, 2005.

Dadhich, Ritesh et al. "Coupled Crystal Plasticity-Phase Field Modeling of Multi-Phase Metals", 2nd International Conference on Structural Integrity and Exhibition 2018, Procedia Structural Integrity, vol. 14, pp. 104-111, Jan. 1, 2019.

Lim, Hojun et al. "Incorporating Physically-based Microstructures in Materials Modeling: Bridging Phase Field and Crystal Plasticity Frameworks", Modelling and Simulation in Materials Science and Engineering, vol. 24, No. 4, p. 045016 (19 pages), Apr. 25, 2016.

Lim, H. et al. "Grain-scale Experimental Validation of Crystal Plasticity Finite Element Simulations of Tantalum Oligocrystals", International Journal of Plasticity, vol. 60, pp. 1-18, Sep. 1, 2014.

Luan, Qinmeng et al. "Combining Microstructural Characterization With Crystal Plasticity and Phase-Field Modelling for the Study of Static Recrystallization In Pure Aluminium", Computational Materials Science, vol. 173, pp. 1-14, Nov. 25, 2019.

European Search Report for Application No. EP 21203646.1, two pages, dated Apr. 27, 2022.

Extended European Search Report for Application No. EP 21203646. 1, 15 pages, dated May 24, 2022.

Fan X G et al., "Through-process macro-micro finite element modeling of local loading forming of large scale complex titanium allow component for microstructure prediction", Journal of Materials Processing Technology, vol. 214, 2014, pp. 253-266.

Bimal K Kad et al., "Computational modeling of through-thickness dynamic impact response in cross-rolled Ti—6Al—4V plates", Metallurgical and Materials Transactions A, vol. 33A, 2002, pp. 937-947.

Ghamarian I et al., "Developing a phenomenological equation to predict yield strength from composition and microstructure in [beta] processed Ti—6Al—4V", Materials Science & Engineering A, vol. 660, 2016, pp. 172-180.

Combined Search and Examination Report for GB2100964.2 dated Oct. 19, 2021, 11 pages.

\* cited by examiner

METHOD OF MODELLING OF A MATERIAL

CROSS RELATED APPLICATION

This application claims priority to India Patent Application 202011052043, filed Nov. 30, 2020, the entire contents of which is hereby incorporated by reference.

FIELD OF THE INVENTION

The present invention relates to a method of predicting a mechanical property of a material subjected to a microstructural transformation, a computer-readable medium for executing said method, a component obtainable via a microstructural transformation based upon said method and a system for performing said method.

BACKGROUND OF THE INVENTION

The development of new materials processes, particularly those proposed for use in safety-critical applications, can be an extremely costly and time-consuming exercise.

In fact, the development of new materials processes requires extensive experimentation and laboratory time for determining how various compositions respond to different processing conditions and for optimising process parameters based on the results of experimentation, typically using trail-and-error based methodologies.

Furthermore, once a desirable set of parameters has been achieved, there is a further need to validate said results which further increases the lead time and costs incurred when developing such processes.

It is therefore the aim of the present invention to provide a means for reducing the laboratory time (and associated costs) incurred when developing and optimising new materials processes.

SUMMARY OF THE INVENTION

According to a first aspect of the claimed invention, there is provided a method of predicting a mechanical property of a material subjected to a microstructural transformation, the method comprising a modelling step, wherein a microstructural model of the material is created for predicting the microstructural evolution of the material upon subjection to a microstructural transformation, a simulation step, wherein the microstructural model of the material created during the modelling step is virtually subjected to a microstructural transformation, a generation step, wherein at least one micro-scale model configured for predicting at least one mechanical property of the material based on the microstructural model is generated and a characterising step, wherein a virtual characterisation is performed on the microstructural model using the at least one micro-scale model generated during the generation step, so as to predict at least one mechanical property of the material virtually subjected to the microstructural transformation.

The at least one micro-scale model may be a crystal plasticity simulation model. The virtual characterisation may be a crystal plasticity simulation.

The microstructural model may be a multi-phase field model.

The microstructural transformation simulated as part of the simulation step may be a heat treatment process. The microstructural transformation simulated as part of the simulation step may be a thermo-mechanical process.

The microstructural model is created based on image data. The image data may be obtained via at least one of X-Ray Diffraction; Scanning Electron Microscope (SEM) microscopy; Transmission Electron Microscope (TEM) microscopy and/or Electron Back Scattering.

The image data may comprise a plurality of images.

The modelling step may comprise estimating a probability distribution for at least one of a grain size, a grain orientation, a grain shape and/or a percentage of alpha and beta phase material based on the image data. The simulation performed as part of the simulation step may comprise performing a probabilistic simulation using the probability distribution estimated during the modelling step.

The image data may be obtained from at least two different viewpoints.

The modelling step may comprise extracting an upper and/or lower bound of at least one of a grain size, a grain orientation, a grain shape and/or a percentage of alpha and beta phase material from the image data. The simulation performed as part of the simulation step may be performed using the upper and/or lower bound data extracted during the modelling step.

The simulation step may comprise simulating the effects of the microstructural transformation on at least one of a grain size and/or a grain density of the microstructural model.

The characterising step may comprise predicting at least one of a tensile strength, a compressive strength, a plasticity and/or a fracture toughness of the material virtually subjected to the microstructural transformation.

The method may comprise a simulation validation step, wherein the microstructural transformation simulated in the simulation step is physically performed on a sample of the material, a first comparison step, wherein the microstructure observed following the simulation validation step is compared to the microstructure predicted during the simulation step and a first feedback step, wherein the microstructural model is adjusted based upon the results of the first comparison step.

The method may comprise a characterisation validation step, wherein the mechanical characterisation simulated using the at least one micro-scale model is physically performed on a sample of the material, a second comparison step, wherein the mechanical properties of the material determined during the characterisation validation step are compared to the mechanical properties of the material predicted via the virtual mechanical characterisation and a second feedback step, wherein the at least one micro-scale model is adjusted based upon the results of the second comparison step.

The material may be an additively manufactured material. The method may further comprise, prior to the modelling step, a solidification modelling step wherein the solidification of the material during the additive manufacturing process is simulated. The additive manufacturing process may be one of Electron Beam Melting, Wire Feed Melting and/or Selective Laser Sintering. The simulation performed as part of the solidification modelling step may be performed using a multi-phase field model.

The material may be an alloy material. The alloy material may be a titanium-based alloy material. The titanium-based alloy material may be a metastable or near beta titanium-alloy material. The alloy material may be one of: Ti-17, Ti-5553, Ti-35Nb-7Zr-5Ta, Ti-10-2-3, Ti-35Nb-5Ta-7Zr, Ti-29Nb-13Ta-4.6Zr, Ti-15V-3Cr-3Al-3Sn, Ti-15Mo-3Nb-3Al-0.2Si, Ti-15Mo, Ti-3Al-8V-6Cr-4Mo-4Zr, Ti-12Mo-6Zr-2Fe or Ti-13V-11Cr-3Al.

The simulation step may comprise virtually heating the microstructural model to a temperature above a beta transus temperature of the material.

The simulation step may comprise virtually heating the microstructural model to a temperature below a beta transus temperature of the material.

According to a second aspect of the claimed invention, there is provided a computer-readable medium for executing the method according to any preceding claim.

According to a third aspect of the claimed invention, there is provided a component obtainable via a microstructural transformation process based upon the method of the first aspect of the claimed invention.

In exemplary embodiments, the component is an aircraft component.

In exemplary embodiments, the component is one of a billet, a bloom, an ingot.

In exemplary embodiments, the component is an additively manufactured component.

According to a fourth aspect of the claimed invention, there is provided a system for predicting a mechanical property of a material according to the method of the first aspect of the claimed invention.

The term "microstructural transformation" refers to any process in which the microstructure of a given material is altered. This can include heat treatment processes, thermo-mechanical processes as well as other materials processes which cause a change to the microstructure of a material.

The term "primary microstructure" refers to the micro-structure of the material before any processing has been carried out on the material.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
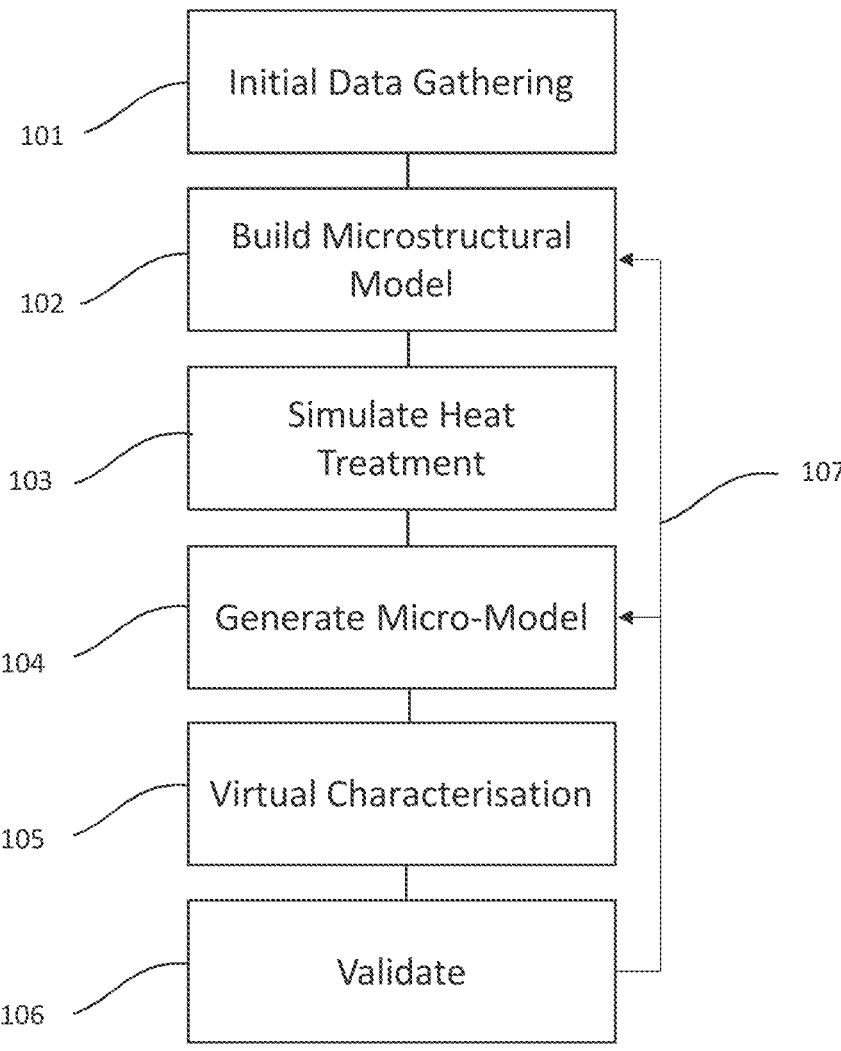
FIG. 1 is a flow chart illustrating a method of predicting a mechanical property of a material according to a first embodiment.

FIG. 1 illustrates a method of predicting a mechanical property of a material according to a first embodiment of the present invention.

In a first step 101 of the illustrated method, the primary microstructure of the material is determined in order to provide baseline data upon which a microstructural model can be based.

Typically, the step of determining the primary microstruc-ture of the material is carried out using laboratory charac-terisation techniques whereby imaging data of a sample of said material is obtained to enable accurate modelling of the primary microstructure. For example, if the method is being used for predicting the mechanical properties of a billet of Ti-64 alloy material, then the primary microstructure of said alloy will be determined based on imaging data obtained via performing laboratory characterisation experiments on samples of Ti-64 alloy material stock.

Typically, the primary microstructure of the material is determined using imaging data obtained using one, or a combination of, X-Ray Diffraction, Scanning Electron Microscope (SEM) microscopy, Transmission Electron Microscope (TEM) microscopy and/or Electron Back Scat-tering. However, it will be appreciated that, in other embodi-ments, other suitable methods, such as standard microscopy, may be used.

It has been found that by performing laboratory charac-terisation, such as the steps specified above, and then incorporating the resulting imaging data from these experi-ments into the microstructural model, it is possible to more accurately model the real-life behaviour of the material during the simulation (as will be described in greater detail below). This in turn helps to more accurately predict the mechanical properties of the material based on the micro-structural model.

However, it shall also be appreciated that when modelling materials which already have a known primary microstruc-ture, the step of determining the primary microstructure of the material may be performed via referencing data that is already available from existing literature, rather than via performing an independent laboratory characterisation.

Once the primary microstructure of the material has been determined in step 101, a microstructural model is created at step 102 for simulating the microstructural evolution of the material upon subjection to a microstructural transformation (such as a heat treatment or thermos-mechanical process).

Typically, the microstructural model is a multi-phase field model of a billet, bloom or ingot created based on the data obtained during step 101. However, it shall be appreciated that in other embodiments, other suitable model types may be used.

In the illustrated embodiment, the data obtained during step 101 is run through a suitable conversion software so as to convert the data into a computational model, in this case a multi-phase field model. In the illustrated embodiment, MATLAB® software was used for performing this conver-sion, although it shall be appreciated that in other embodi-ments, other suitable software may be used.

Whilst it is possible to input only a single image into the conversion software in order to obtain the computational model, more typically a plurality of images (often in the order of magnitude of 100) are input into the conversion software in order to obtain the computational model.

From this image data, the conversion software is able to extract values for properties of the material such as the grain size, grain orientation, grain shape and/or morphology and also the percentage of alpha and beta phases for a given material which can be implemented into the microstructural model. By using an increased amount of data when creating such models, it is possible to more accurately represent the real-world behaviour of such alloys.

Typically, the values extracted from the image data are used to estimate a probability distribution for the various properties of the material, such as the grain size, grain orientation, grain shape and/or morphology and also the percentage of alpha and beta phases.

During the simulation step, as will be described in greater detail below, the estimated probability distributions can then be used to perform probabilistic simulations, wherein multiple simulations are performed using various inputs which are randomly selected from within the probability distribution. This helps the microstructural model to better account for uncertainties in the data which can result due to factors such as measurement uncertainty, spatial in-homogeneity, variation of loads on the microstructure, as well as others.

Furthermore, by obtaining a results distribution, the optimal properties of an alloy can be more efficiently determined.

However, it shall be appreciated that in other embodiments, other modelling and simulation methods may be used.

It shall also be appreciated that the use of probability distributions to obtain input values for simulations and the use of probabilistic simulations may also be implemented in other aspects of the described method.

Furthermore, in some embodiments, an upper and/or lower bound of the data set may be extracted for a given material to be used as input data during the simulation.

In the illustrated embodiment, the microstructural model is shown as a two-dimensional model and so each image used to obtain the microstructural model may be taken from a single viewpoint such as a plan view image showing the X-Y plane of the material.

However, it shall be appreciated that in other embodiments, the microstructural model may be a three-dimensional model and so the images used to obtain the microstructural model may be taken from multiple viewpoints (such as a plan view image showing the X-Y plane of the microstructure, and a side view image showing the Y-Z plane of the microstructure) to enable a three-dimensional microstructural model to be obtained for a given microstructure.

Figure 2A:
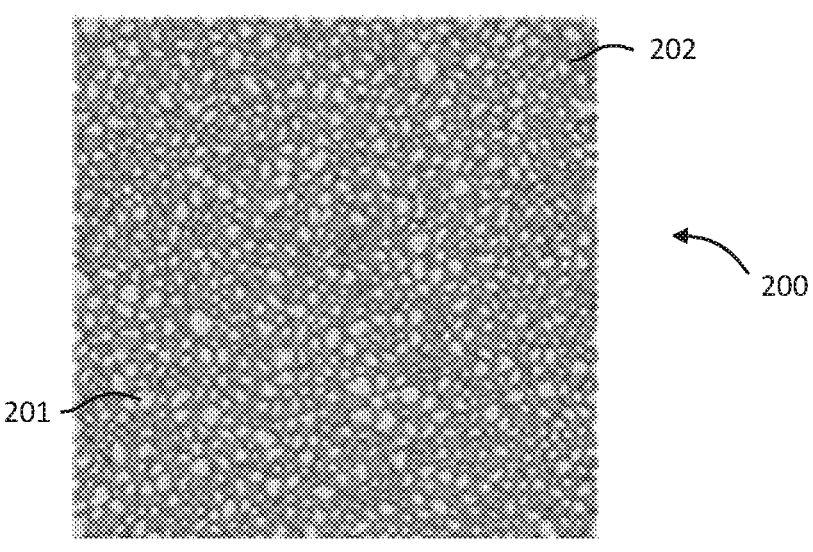
FIG. 2a is an image depicting the microstructure of a Ti-64 sample.

In the illustrated embodiment, the material of interest is an alpha plus beta titanium alloy material, such as Ti-64. As can be seen in FIG. 2a, Ti-64 typically exhibits a microstructure 200 featuring equiaxed grains of primary alpha 201 and transformed beta 202 titanium. As such, the microstructural model 210, shown in FIG. 2b, which provides a virtual representation of the microstructure of the Ti-64 sample, subsequently features a series of titanium grains 211, 212, 213 with respective interfaces 214, 215, 216 located therebetween.

However, it shall be appreciated that in other embodiments, metastable or near beta titanium alloys, such as Ti-17, Ti-5553, Ti-35Nb-7Zr-5Ta, Ti-10-2-3, Ti-35Nb-5Ta-7Zr, Ti-29Nb-13Ta-4.6Zr, Ti-15V-3Cr-3Al-3Sn, Ti-15Mo-3Nb-3Al-0.2Si, Ti-15Mo, Ti-3Al-8V-6Cr-4Mo-4Zr, Ti-12Mo-6Zr-2Fe or Ti-13V-11Cr-3Al may be modelled, and so in other embodiments the microstructural model may be provided in a different form to that which has been described above.

Figure 2B:
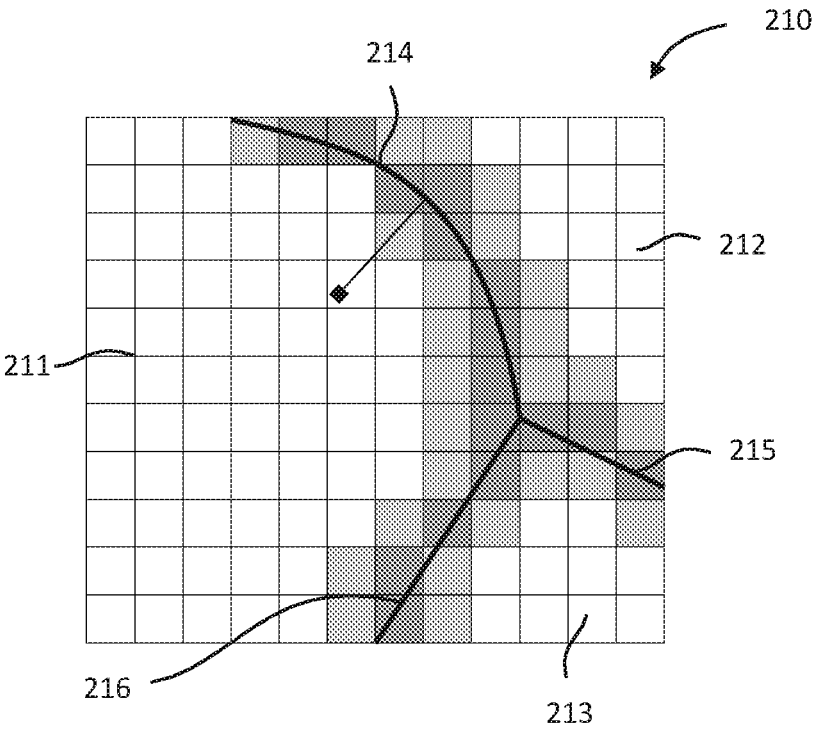
FIG. 2b is a schematic illustration of a microstructural model for modelling the microstructural evolution of a sample of Ti-64 alloy material subjected to a heat treatment process.

For example, near-beta titanium alloys tend to exhibit extensive beta-phase "basket-weave" microstructures with small pockets of alpha-phase precipitate being dispersed therebetween, and so microstructural models of near-beta titanium alloys are likely to vary significantly from that which is shown in FIG. 2b.

It shall also be appreciated that in other embodiments, the material of interest may be a different material, and as such it shall be appreciated that the illustrated methodology is not limited solely to titanium modelling applications.

The shape and distribution of grains are represented by a set of functions, also known as phase-field variables. The phase-field variables are assigned values which relate to the structure, orientation and composition of the grains 211, 212, 213. As specified above, in some examples, said values may include values for the grain size, grain orientation, grain shape and/or morphology and also the percentage of alpha and beta phases for a given material, although it shall be appreciated that other suitable values may be used. The respective interfaces 214, 215, 216 are defined by the area between the grains 211, 212, 213.

As the phase-field variables evolve (i.e. gradually change) as a function of time, the respective shape of the grains 211, 212, 213 and the position of the respective interfaces 214, 215, 216 will also evolve accordingly thereby enabling the model to simulate the microstructural evolution that would be experienced by a real-life sample of material undergoing the same microstructural transformation in the real-world. This modelling approach is sometimes called as "diffuse-interface description". Suitable types of software that is available for performing this kind of modelling include MiCRESS®, DICTRA, Open Phase, JMatPro® as well as others.

The temporal evolution of the phase field variables is described by a set of partial differential equations. The partial differential equations typically consider driving forces for micro-structural evolution such as reduction in bulk energy, interfacial energy and elastic energy, although it shall be appreciated that other such factors may be considered in some embodiments.

An example of a typical set of partial equations for modelling the diffusion controlled alpha phase growth within is beta matrix is provided below.

$$\frac{\partial c^{\alpha}}{\partial t} = D^{\alpha} \nabla^{\alpha} c^{\alpha} \tag{1}$$

$$\frac{\partial c^{\beta}}{\partial t} = D^{\beta} \nabla^{\beta} c^{\beta} \tag{2}$$

$$(c^{\alpha,int} - c^{\beta,int}) = D^{\beta} \frac{\partial c^{\beta}}{\partial r_1} - D^{\alpha} \frac{\partial c^{\alpha}}{\partial r_1} \tag{3}$$

$$\mu^{\alpha}(c^{\alpha,int}) = \mu^{\beta}(c^{\beta,int}) \tag{4}$$

wherein $c^{\alpha}$ and $c^{\beta}$ are the molar concentrations of the solute element in the $\alpha$-phase and the $\beta$-phase respectively, $D^{\alpha}$ and $D^{\beta}$ are the diffusion coefficients, $c^{\alpha,int}$ and $c^{\beta,int}$ are the molar concentrations of the solute element at the interface and $\mu^{\alpha}$ and $\mu^{\beta}$ represent the chemical potentials of the solute for the $\alpha$-phase and the $\beta$-phase respectively.

Typically, the aforementioned thermodynamic equations and constants are applied to only a single grain of the model which can then be extrapolated to the remaining grains during the simulation. This helps to reduce the data processing burden placed upon the model and hence enables simulations to be performed more quickly and efficiently.

However, it shall be appreciated that in other embodiments, the aforementioned thermodynamic equations and constants may be applied to multiple grains of the model to help reduce the amount of extrapolation required, and to thereby further improve the accuracy of the model, albeit at the expense of adding an additional data processing burden to the model.

Once the microstructural model 210 has been created during step 102, a simulation is performed during step 103, wherein the microstructural model 210 created during the modelling step 102 is virtually subjected to a microstructural transformation. In this manner, it is possible to virtually subject the microstructural model of the material to a treatment process, during which the predicted microstructural evolution of the material can be observed.

Figure 3:
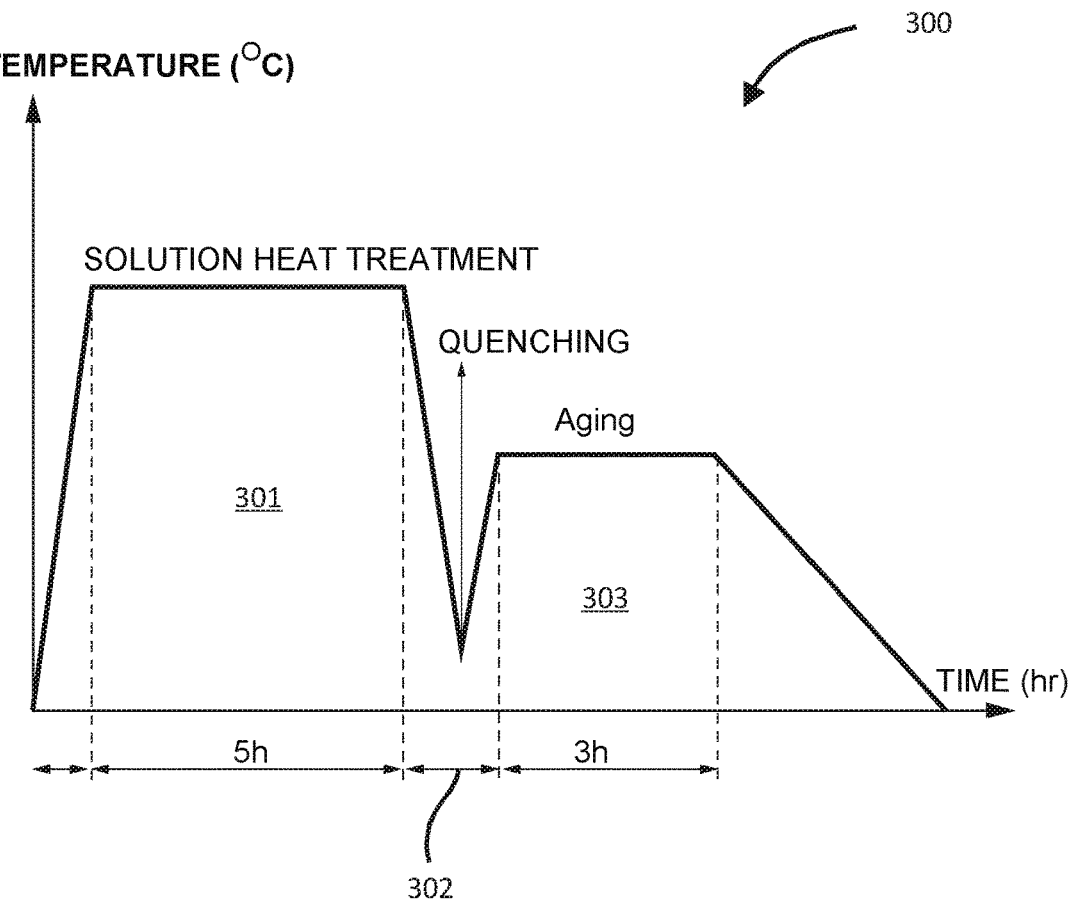
FIG. 3 is a Gantt chart depicting the heat treatment process simulated during the method illustrated in FIG. 1.

In the embodiment illustrated in FIG. 1, the simulated microstructural transformation is a solution treatment 301 wherein a Ti-64 billet is heated to a temperature above a beta transus temperature of the Ti-64 alloy material followed by a quenching 302 and ageing 303 treatment, performed below the beta transus temperature of the Ti-64 alloy, as shown in FIG. 3. However, it shall be appreciated that in other embodiments, other kinds of transformation (for example a thermo-mechanical process such as rolling or forging) may be simulated during step 103. It is also important to note that whilst the aforementioned embodiment is described in relation to a titanium alloy, it shall be appreciated that the method may be applied to any suitable material type.

Following the simulation step 103, the microstructural model is in a state which mimics the final microstructure which would be expected to be obtained following the afore-described heat treatment process being performed on a real-life billet of a Ti-64 alloy material. As such, it is possible to use this simulated microstructure to help predict the mechanical properties of such a sample as shall be described below.

At step 104, one or more micro-models are generated to enable the user to predict the mechanical properties of the material subjected to the simulated microstructural transformation.

Figure 5:
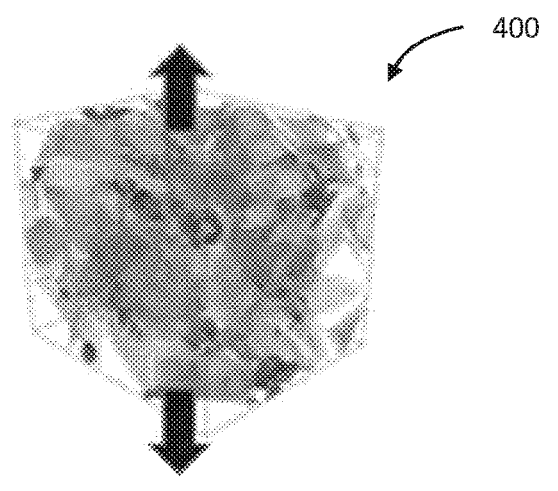
FIG. 5 is a schematic illustration of a micro-scale crystal plasticity simulation model for predicting at least one mechanical property of the material modelled in FIG. 2b.
Figure 4A:
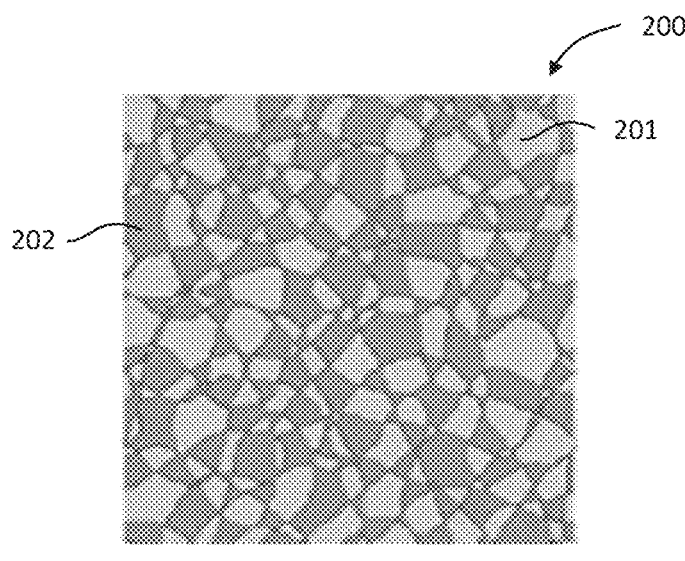
FIG. 4a is a schematic illustration of the microstructure of a sample of Ti-64 alloy material following a solution treatment performed above the beta transus temperature of the material.
Figure 4B:
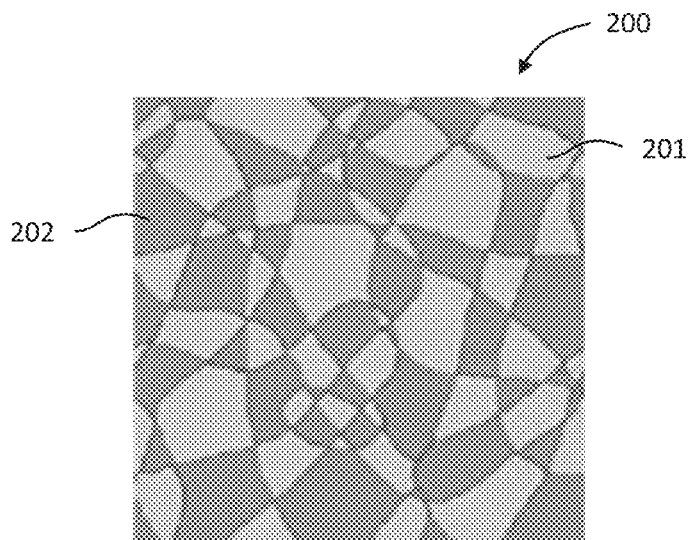
FIG. 4b is an schematic illustration of the microstructure of a sample of Ti-64 alloy material following an ageing treatment performed below the beta transus temperature of the material.

In the illustrated embodiment, the at least one micro-scale model 400 is a crystal plasticity simulation model, as illustrated in FIG. 5, which is configured for predicting at least one mechanical property of the material based on the microstructural model 210, such as tensile strength, compressive strength, plasticity and/or fracture toughness of the material. However, it shall be appreciated that in other embodiments, any other suitable model type may be used.

Similarly to the microstructural model described during step 102, a set of relevant boundary conditions and materials constants are input into the micro-scale model. The materials constants for being input into the micro-scale model can be determined experimentally prior to generation of the model, or can be obtain based on data available from existing literature.

Once the micro-scale model (or models) have been generated in step 104, a virtual mechanical characterisation 105 can be performed using the at least one micro-scale model 400 generated during the generation step 104, so as to predict at least one mechanical property of the material subjected to the microstructural transformation (in this case a heat treatment process).

In the illustrated embodiment, the virtual mechanical characterisation 105 is a crystal plasticity simulation performed using the crystal plasticity simulation model, which enables the model to predict one or more mechanical properties of the material subjected to the microstructural transformation. However, it shall be appreciated that in other embodiments, other mechanical properties of the material may be predicted.

An example of one possible virtual mechanical characterisation that can be performed using the micro-scale model 400 is a virtual tensile test as would ordinarily be performed in a laboratory according to ASTM D638 protocols.

ASTM D638 protocol tensile tests typically involve a "dog-bone" specimen being secured between respective arms of a Universal Testing Machine (or UTM) which applies a tensile load to the specimen. Upon analysing the amount of lengthening undergone by a specimen during said test, as well as the respective failure point of the material, it is possible to obtain the stress/strain characteristics of the material which can be plotted on a stress-strain curve.

As such, when simulating a tensile test of this kind, the boundary conditions of the micro-scale model can be set during the virtual mechanical characterisation so as to mimic a tensile load being applied to the material, as shown in FIG. 5. Consequently, by monitoring the degree of grain deformation undergone by the micro-scale model 400 in response to the application of a virtual tensile load, a stress-strain curve can be obtained for the material being subjected to the virtual mechanical characterisation which can, in turn, enable the user to more accurately predict the mechanical properties of such a material.

As such, by simulating the microstructural evolution of the material during microstructural transformation and then performing a virtual mechanical characterisation of the material subjected to said transformation, it is possible to predict the effects of the material transformation processes on the mechanical properties of the material without requiring significant laboratory time.

Furthermore, the parameters of the model can be easily adjusted once the model has been created which subsequently enables a large number of transformations to be simulated without requiring significant user input or laboratory time.

In this way, the laboratory time and research costs incurred when developing and optimising such processes can be significantly reduced.

Furthermore, validation processes, such as the validation step 106, can be performed at each step of the method and the results of these validation processes can be fed back into the model to help better ensure the accuracy of the model.

For example, in order to validate the heat treatment simulation performed during step 103, a corresponding heat treatment process using a real sample of the material, in this case Ti-64, may be performed in a laboratory (or foundry) in order to verify the results of the simulation.

The microstructure obtained via the real-world heat treatment process can then be compared to the microstructure predicted by the simulated heat treatment process and, should any discrepancies be observed, suitable changes can be incorporated into the equations and data underpinning the microstructural model during a feedback step 107 to help better ensure accuracy of the model for future simulations.

In another example, one or more samples of the material may also be prepared for tensile testing during the validation step to enable the actual mechanical properties of the material processed according to the simulated heat treatment to be determined.

As specified above, in the illustrated embodiment, the mechanical properties of the material predicted during the virtual mechanical characterisation 105 include a tensile strength of the material. As such, the testing step in this instance may involve performing one or more tensile tests, for example using ASTM D638 protocols, on one or more samples processed using the same heat treatment process as that which has been simulated via the microstructural model to determine whether the actual tensile strength exhibited by the samples matches the tensile strength predicted by the model so as to further verify the results of the simulation.

Details of suitable tension tests and how they are performed are well known in the art and so, for the sake of conciseness, shall not be described in any further detail. It shall also be appreciated that similar testing protocols may also be used for determining properties such a compressive strength and/or fracture toughness of the sample.

The micro-scale model can then be adjusted should any discrepancies be observed between the mechanical properties determined via real-world testing and the mechanical properties predicted via the simulation during the feedback step 107 to help better ensure accuracy of the model for future simulations. In this manner, the accuracy of the simulation can be further improved.

Figure 6:
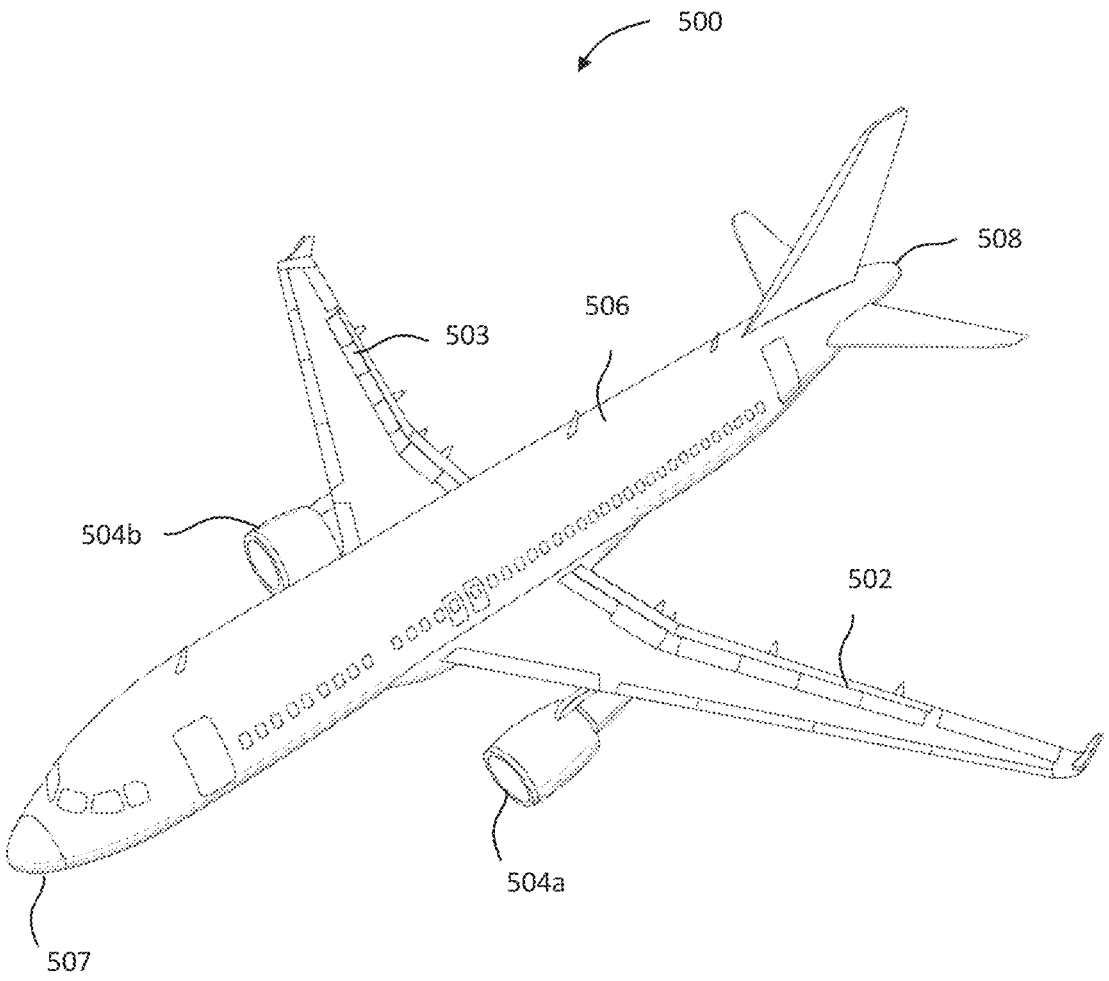
FIG. 6 is a perspective view of an aircraft schematically illustrating one potential application for a component manu-factured based upon the results of the method according to the embodiment illustrated in FIG. 1.

In the illustrated embodiment, the transformation process is a heat treatment process envisaged for treating components suitable for use on an aircraft. FIG. 6 illustrates an aircraft 500 which is one potential application for a component manufactured based upon the results of the method according to the embodiment illustrated in FIG. 1.

The aircraft 500 illustrated in FIG. 6 is a fixed wing aircraft 500 having a port wing 502 and starboard wing 503 carrying wing mounted engines 504*a*, 504*b* respectively. The wing mounted engines 504*a*, 504*b* are attached to the respective port and starboard wings via pylons (not shown).

Each wing 502, 503 of the aircraft 500 has a cantilevered structure with a length extending in a span-wise direction from a root to a tip, the root being joined to an aircraft fuselage 506. However, it will be appreciated that the fuselage 506 and wings 502, 503 may take a variety of different planform shapes and profiles depending on the particular application.

The fuselage 506 has a nose 507 and a tail 508, which forms the empennage of the aircraft 500, where respective horizontal and vertical stabilisers of the aircraft 500 are located.

However, it shall be appreciated that components for use in other applications may also be obtained via a transformation process based on the afore-described method.

As has been mentioned above, the method according to the first embodiment of the present invention provides a means for predicting the mechanical properties of a material subjected to a microstructural transformation, wherein the starting material stock (which is to undergo the simulated heat treatment process) is provided in the form of a billet, a bloom or an ingot.

However, it shall also be appreciated that the method for predicting the mechanical properties of a material subjected to a microstructural transformation can also be used for processes wherein the starting material stock is provided in the form of an additively manufactured component.

However, when modelling the microstructural evolution of a material obtained from an additive manufacturing process, it is generally preferable to include an additional simulation step in order to account for the solidification processes which the material undergoes during the additive layer build process, in order to further improve the accuracy of the model.

A method of predicting a mechanical property of an additively manufactured material subjected to a microstructural transformation according to an embodiment of the present invention shall now be described with reference to FIG. 7.

Figure 7:
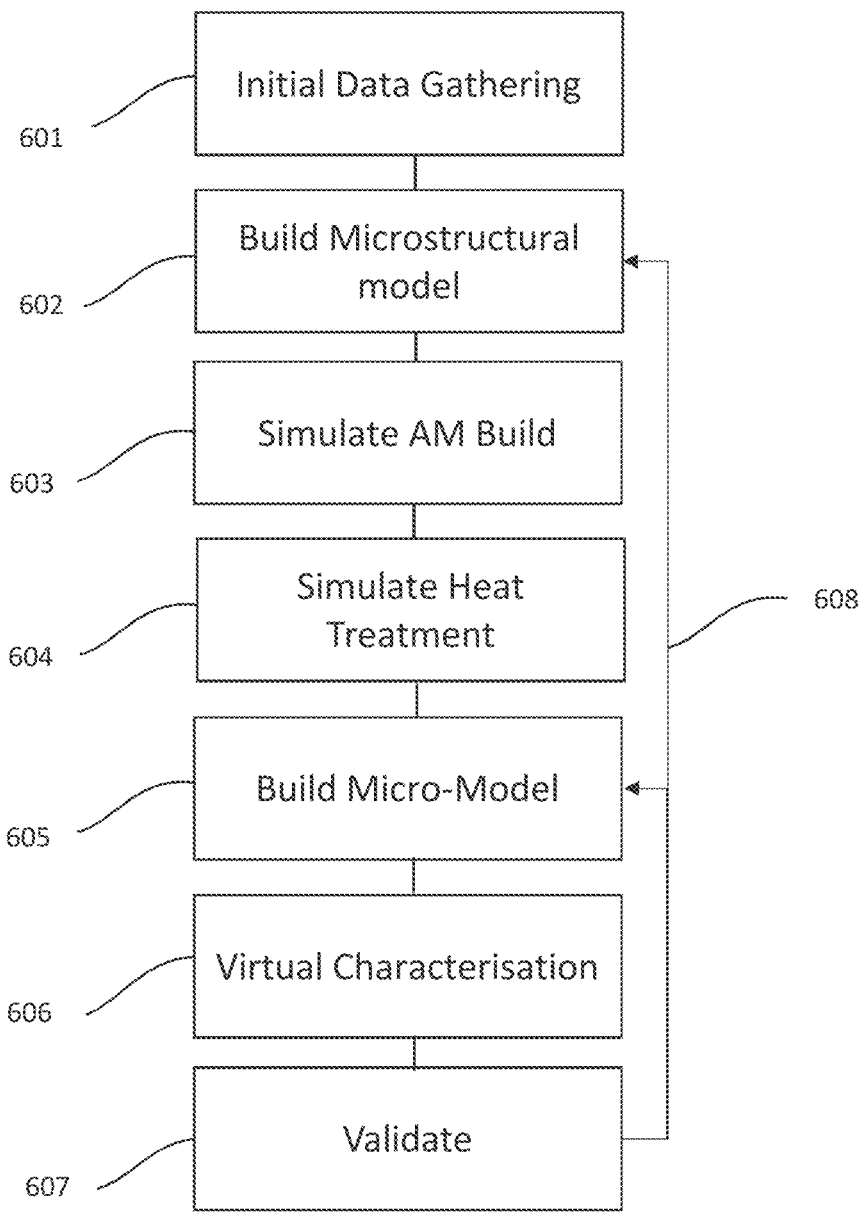
FIG. 7 is a flow chart illustrating a method of predicting a mechanical property of an additively manufactured com-ponent according to an alternative embodiment.

The embodiment illustrated in FIG. 7 depicts a method of predicting the mechanical properties of a material manufactured via an Electron Beam Melting additive manufacturing process. However, in other embodiments, it shall be appreciated that other kinds of additive manufacturing processes, such as Wire Feed Melting and Selective Laser Sintering, may be simulated during this step.

The majority of the method steps described in relation to FIG. 7 are substantially the same as those described in relation to FIG. 1 and so, for the sake of conciseness, only the difference will be described below. However, unlike the method described in relation to FIG. 1, the method according to the embodiment illustrated in FIG. 7 includes a further solidification modelling step 603, prior to the heat treatment simulation step 604, wherein the solidification of the material subjected to the additive manufacturing process from a liquid phase material to a solid phase materials is simulated.

The simulation performed as part of the solidification modelling step 603 is typically performed using the microstructural model generated during the modelling step 602. In the illustrated embodiment, the microstructural model is a multi-phase field model, however it shall be appreciated that in other embodiments, other model types may be used.

By including this additional simulation step, the model is able to better account for any microstructural changes which occur as a consequence of the additive manufacturing process. Advantageously, this helps the model to more accurately predict the mechanical properties of the material.

Although the invention has been described above with reference to one or more preferred embodiments, it will be appreciated that various changes or modifications may be made without departing from the scope of the invention as defined in the appended claims.

Where the word 'or' appears this is to be construed to mean 'and/or' such that items referred to are not necessarily mutually exclusive and may be used in any appropriate combination.

The invention claimed is:

1. A computer-implemented method of predicting a mechanical property of a material subjected to a microstructural transformation, the method comprising:

a modelling step, wherein a microstructural model of the material is created for predicting a microstructural evolution of the material upon subjection to the microstructural transformation;

a simulation step, wherein the microstructural model of the material created during the modelling step is virtually subjected to the microstructural transformation;

a generation step, wherein at least one micro-scale model is generated, and wherein the at least one micro-scale model is configured for predicting at least one mechanical property of the material based on the microstructural model after it has been virtually subjected to the microstructural transformation;

a characterising step, wherein a virtual characterisation is performed on the microstructural model using the at least one micro-scale model generated during the generation step, so as to predict the at least one mechanical property of the material after it has been virtually subjected to the microstructural transformation;

performing a microstructural transformation process on a physical sample of the material, wherein the transformation process is based on the simulated microstructural transformation from the simulation step, and wherein using the transformed sample as a component;

performing validation processes at each step of the method; and feeding back the results of these validation processes into the model in order to help better ensure the accuracy of the model.

2. The method according to claim 1, wherein the at least one micro-scale model comprises a crystal plasticity simulation model and wherein the virtual characterisation comprises a crystal plasticity simulation.

3. The method according to claim 1, wherein the microstructural model comprises a multi-phase field model.

4. The method according to claim 1, wherein the microstructural transformation simulated as part of the simulation step comprises a heat treatment process.

5. The method according to claim 1, wherein the microstructural transformation simulated as part of the simulation step comprises a thermo-mechanical process.

6. The method according to claim 1, wherein the microstructural model is created based on image data.

7. The method according to claim 6, wherein the image data is obtained via at least one of X-Ray Diffraction; Scanning Electron Microscope (SEM) microscopy; Transmission Electron Microscope (TEM) microscopy and/or Electron Back Scattering.

8. The method according to claim 6, wherein the image data comprises a plurality of images, wherein the modelling step comprises estimating a probability distribution for at least one of a grain size, a grain orientation, a grain shape and/or a percentage of alpha and beta phase material based on the image data, and wherein a simulation performed as part of the simulation step comprises performing a probabilistic simulation using the probability distribution estimated during the modelling step.

9. The method according to claim 6, wherein the image data comprises a plurality of images and wherein the image data is obtained from at least two different viewpoints.

10. The method according to claim 1, wherein the image data comprises a plurality of images, wherein the modelling step comprises extracting an upper and/or lower bound of at least one of a grain size, a grain orientation, a grain shape and/or a percentage of alpha and beta phase material from the image data, and wherein a simulation performed as part of the simulation step is performed using the upper and/or lower bound data extracted during the modelling step.

11. The method according to claim 1, wherein the simulation step comprises simulating effects of the microstructural transformation on at least one of a grain size and/or a grain density of the microstructural model.

12. The method according to claim 1, wherein the characterising step comprises predicting at least one of a tensile strength, a compressive strength, a plasticity and/or a fracture toughness of the material virtually subjected to the microstructural transformation.

13. The method according to claim 1, wherein the method further comprises:

a characterisation validation step, wherein a mechanical characterisation simulated using the at least one micro-scale model is physically performed on a sample of the material;

a second comparison step, wherein the at least one mechanical property of the material determined during the characterisation validation step are compared to the at least one mechanical property of the material predicted via the virtual characterisation; and a second feedback step, wherein the at least one micro-scale model is adjusted based upon the results of the second comparison step.

14. The method according to claim 1, wherein the material is an additively manufactured material, and wherein the method further comprises, prior to the modelling step, a solidification modelling step wherein solidification of the material during the additive manufacturing process is simulated.

15. The method according to claim 14, wherein the additive manufacturing process is one of Electron Beam Melting, Wire Feed Melting and/or Selective Laser Sintering.

16. The method according to claim 14, wherein the simulation performed as part of the solidification modelling step is performed using a multi-phase field model.

17. The method according to claim 1, wherein the material is an alloy material, preferably wherein the alloy material is a titanium-based alloy material and most preferably wherein the titanium-based alloy material is a metastable or near beta titanium-alloy material.

18. The method according to claim 17, wherein the alloy material is one of: Ti-17, Ti-5553, Ti-35Nb-7Zr-5Ta, Ti-10-2-3, Ti-35Nb-5Ta-7Zr, Ti-29Nb-13Ta-4.6Zr, Ti-15V-3Cr-3Al-3Sn, Ti-15Mo-3Nb-3Al-0.2Si, Ti-15Mo, Ti-3Al-8V-6Cr-4Mo-4Zr, Ti-12Mo-6Zr-2Fe or Ti-13V-11Cr-3Al.

19. The method according to claim 17, wherein the simulation step comprises virtually heating the microstructural model to a temperature either above or below a beta transus temperature of the material.

20. A system for predicting a mechanical property of a material comprising a computer configured to perform:

a modelling step, wherein a microstructural model of the material is created for predicting a microstructural evolution of the material upon subjection to a microstructural transformation;

a simulation step, wherein the microstructural model of the material created during the modelling step is virtually subjected to the microstructural transformation;

a generation step, wherein at least one micro-scale model configured for predicting at least one mechanical property of the material based on the microstructural model is generated;

a characterising step, wherein a virtual characterisation is performed on the microstructural model using the at least one micro-scale model generated during the generation step, so as to predict the at least one mechanical property of the material virtually subjected to the microstructural transformation;

performing a microstructural transformation process on a physical sample of the material, wherein the transformation process is based on the simulated microstructural transformation from the simulation step, and wherein using the transformed sample as a component;

performing validation processes at each step of the method; and feeding back the results of these validation processes into the model in order to help better ensure the accuracy of the model.

* * * * *